(12) United States Patent
Regensburger et al.

(10) Patent No.: US 10,838,189 B2
(45) Date of Patent: Nov. 17, 2020

(54) OPERATING MICROSCOPE HAVING AN IMAGE SENSOR AND A DISPLAY, AND METHOD FOR OPERATING AN OPERATING MICROSCOPE

(71) Applicant: Carl Zeiss Meditec AG, Jena (DE)

(72) Inventors: Alois Regensburger, Erlangen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 239 days.

(21) Appl. No.: 15/923,815

(22) Filed: Mar. 16, 2018

(65) Prior Publication Data
US 2018/0267287 A1 Sep. 20, 2018

(30) Foreign Application Priority Data

Mar. 20, 2017 (DE) .......................... 10 2017 105 941

(51) Int. Cl.
| | |
|---|---|
| G02B 21/36 | (2006.01) |
| G02B 23/00 | (2006.01) |
| G02B 21/00 | (2006.01) |
| G02B 21/02 | (2006.01) |
| G02B 21/22 | (2006.01) |
| A61B 3/13 | (2006.01) |

(52) U.S. Cl.
CPC ....... *G02B 21/361* (2013.01); *G02B 21/0012* (2013.01); *G02B 21/025* (2013.01); *G02B 21/22* (2013.01); *G02B 21/365* (2013.01); *G02B 21/368* (2013.01); *A61B 3/13* (2013.01)

(58) Field of Classification Search
CPC ............. G02B 21/365; G01N 21/6458; G01N 21/4795

USPC .......................................................... 359/363
See application file for complete search history.

(56) References Cited

U.S. PATENT DOCUMENTS

| | | | | |
|---|---|---|---|---|
| 5,867,210 A * | 2/1999 | Rod | ...................... | H04N 13/337 348/51 |
| 7,688,503 B2 * | 3/2010 | Hermann | ........... | G02B 21/0012 359/368 |

(Continued)

FOREIGN PATENT DOCUMENTS

| | | |
|---|---|---|
| DE | 102 43 852 A1 | 1/2004 |
| DE | 10 2007 019 335 B3 | 9/2008 |

(Continued)

*Primary Examiner* — William R Alexander
*Assistant Examiner* — Tamara Y. Washington
(74) *Attorney, Agent, or Firm* — Falk Ewers; Ewers IP Law PLLC

(57) ABSTRACT

An operating microscope produces an observation image of an object region for an observer. The operating microscope has an eyepiece for observing the observation image of the object region in an intermediate image plane and it contains an imaging optical unit for producing an optical image of the object region in the intermediate image plane by way of an optical object region imaging beam path that is guided from the object region into the intermediate image plane. In the operating microscope, there is a switchable optical assembly for selectively clearing and interrupting the optical object region imaging beam path and an image sensor for capturing an image of the object region by way of an optical image sensor beam path that is guided from the object region to the image sensor.

6 Claims, 10 Drawing Sheets

(56) References Cited

U.S. PATENT DOCUMENTS

| | | | | |
|---|---|---|---|---|
| 8,427,743 B2* | 4/2013 | Sander | ............... | G02B 21/0012 359/353 |
| 2012/0056996 A1* | 3/2012 | Sander | ................. | G02B 21/16 348/47 |
| 2016/0357003 A1* | 12/2016 | Hauger | .............. | G02B 21/0012 |

FOREIGN PATENT DOCUMENTS

| | | |
|---|---|---|
| DE | 10 2010 044 502 A1 | 3/2012 |
| DE | 10 2014 207 130 A1 | 8/2015 |

* cited by examiner

OPERATING MICROSCOPE HAVING AN IMAGE SENSOR AND A DISPLAY, AND METHOD FOR OPERATING AN OPERATING MICROSCOPE

CROSS-REFERENCE TO RELATED APPLICATION

This application claims priority to German patent application DE 10 2017 105 941.5 filed on Mar. 20, 2017, the entire content of which is incorporated herein by reference.

TECHNICAL FIELD

The invention relates to an operating microscope for producing an observation image of an object field in an object region for an observer, having at least one eyepiece for observing the observation image of the object field in the object region in an intermediate image plane, having an imaging optical unit for producing an optical image of the object field in the object region in the intermediate image plane having an optical object region imaging beam path that is guided from the object region into the intermediate image plane along an optical transmission path, having a switchable optical assembly for selectively clearing and interrupting the optical object region imaging beam path, the optical assembly clearing the optical transmission path in a first switching state and interrupting the optical transmission path in a further switching state that differs from the first switching state, having at least one image sensor for capturing an image of the object region by way of an optical image sensor beam path that is guided from the object region to the image sensor, having a display for visualizing display information in the intermediate image plane along a display imaging beam path, and having an image processing and control device for actuating the display and for processing and outputting image data of the image sensor onto the display, having an imaging scale setting device for setting an imaging scale, dependent on the switching state of the optical assembly, for the display information that is visualizable in the intermediate image plane by the display, and having a coupler for coupling the switchable optical assembly and the imaging scale setting device. Moreover, the invention relates to a method for operating an operating microscope.

BACKGROUND

U.S. Pat. No. 8,427,743 B2 describes an operating microscope of the type set forth at the outset.

Operating microscopes are used in different medical disciplines, such as neurosurgery, minimally invasive surgery or else ophthalmology, for example. In particular, they serve to allow an operating physician to observe an operating region with magnification.

US 2016/0056996 A1 describes an operating microscope, which allows an observer to visualize image data displayed on a display in overlaid fashion on the image of the object region in an eyepiece. To this end, the operating microscope contains a beam splitter arranged in the optical object region imaging beam path. This beam splitter mirrors an image of the object region displayed by a display into the optical object region imaging beam path, the image being captured by an image sensor in a characteristic wavelength range.

Operating microscopes, which allow an observer to visualize image data displayed on a display in overlaid fashion on the image of the object region in an eyepiece, the eyepiece providing an optical observation beam path from an object region, are also described in US 2012/0056996 A1 and U.S. Pat. No. 7,688,503 B2.

U.S. Pat. No. 5,867,210 describes an operating microscope system containing an image sensor device, which digitally captures the image of the operating region and displays the image on screens and smartglasses.

SUMMARY

It is an object of the invention to provide an operating microscope which allows an observer to visualize an object region with the same imaging scale, selectively by way of an optical object region imaging beam path and by way of an optical-electronic-optical display imaging beam path, in which images of an image region captured with an image sensor are displayed.

This object is achieved by an operating microscope and a method as disclosed herein.

Displays and image sensors with an installation size suitable for operating microscopes are currently only available with pixel numbers that do not allow an optical resolution of image information corresponding to natural vision.

Against this background, the invention exploits the fact that the visualization of an object region in an eyepiece by way of an optical object region imaging beam path offers the advantage in an operating microscope that a surgeon can observe an operating region with both a very good optical imaging quality and a natural visual impression with color fidelity, even in the case of a high magnification. Secondly, the invention exploits the fact that the digital capture and display of object structures in an operating region is advantageous in numerous applications of operating microscopes. This is because, firstly, comparatively little illumination light is required for the digital capture and display of object structures in an operating region such that this reduces the radiation exposure of body tissue, in particular. The digital capture and display of object structures in an operating region also allows tissue structures which cannot even be captured in the spectral range of visible light to be displayed for an observer.

Moreover, the invention exploits the fact that the visualization of data that were digitally captured using an image capture device and subsequently prepared in a computer unit, for example for increasing an image contrast, may simplify the orientation in an operating region for a surgeon and may also improve the handling of an operating microscope.

The invention combines the advantages of the visualization of an object region with an optical transmission path for image information with the advantages of an object region visualization, which is effectuated by way of an optical-electronic-optical transmission path for image information.

An operating microscope according to an aspect of the invention for producing an observation image of an object region for an observer has at least one eyepiece for observing the observation image of the object region in an intermediate image plane and it contains an imaging optical unit for producing an optical image of the object region in the intermediate image plane by way of an optical object region imaging beam path that is guided from the object region into the intermediate image plane. In an operating microscope according to another aspect of the invention, there is a switchable optical assembly for selectively clearing and interrupting the optical object region imaging beam path and at least one image sensor for capturing an image of the object region by way of an optical image sensor beam path that is guided from the object region to the image sensor. An operating microscope according to an aspect of the invention has a display for visualizing display information in the intermediate image plane by way of a display imaging beam path and contains an image processing and control device for actuating the display and for processing and outputting image data of the image sensor onto the display. In an operating microscope according to a further aspect of the invention, there is an imaging scale setting device for setting an imaging scale, dependent on the switching state of the optical assembly, for the display information that is visualizable in the intermediate image plane on the display.

An operating microscope according to yet another aspect of the invention contains a coupler for coupling the switchable optical assembly and the imaging scale setting device. What this can achieve is that the imaging scale of an object region image perceivable by an observer in an intermediate image plane is automatically set depending on the switching state of the switchable optical assembly.

The imaging scale setting device has an optical magnification interchange system, which is arranged in the image sensor beam path. Here, the magnification interchange system is a constituent part of the imaging optical unit for producing an optical image of the object region in the intermediate image plane. In particular, the magnification interchange system may be an afocal zoom system.

The imaging scale setting device can have a data processing stage integrated into the image processing and control device. Alternatively, or in addition thereto, the imaging scale setting device can also have an optical magnification interchange system, which is arranged in the display imaging beam path.

The switchable optical assembly for selectively clearing and interrupting the optical object region imaging beam path can be embodied, in particular, as a switchable shutter.

Expediently, an operating microscope according to the invention is embodied as a stereoscopic operating microscope.

The invention also extends to a method for operating an operating microscope, as specified above, for the production of an observation image of an object region for an observer, in which the imaging scale for the display information that is visualizable in the intermediate image plane on the display is set depending on the switching state of the optical assembly.

Here, it is an aspect of the invention that the imaging scale is set by adjusting an optical magnification interchange system arranged in the image sensor beam path. A further aspect of the invention is that the imaging scale is provided on the display by displaying display information that has been magnified or reduced in an image processing and control device. In particular, it is an aspect of the invention that the imaging scale is set by adjusting an optical magnification interchange system arranged in the image sensor beam path.

Here, in a first step, an image of the object region can be produced in the intermediate image plane by way of an optical transmission path for image information from the object region into the intermediate image plane and then, in a second step following the first step, an image of the object region can be produced in the intermediate image plane by way of an optical-electronic-optical transmission path for image information from the object region into the intermediate image plane, wherein the imaging scale $M_E$ of the optical-electronic-optical transmission path is set to the imaging scale $M_O$ of the optical transmission path.

When setting the imaging scale $M_E$ of the optical-electronic-optical transmission path, the display of display information on the display is suppressed as far as possible. As an alternative thereto, it is also possible that, when setting the imaging scale $M_E$ of the optical-electronic-optical transmission path, the display of display information on the display is effectuated with an imaging scale matched to the magnification of an optical magnification interchange system arranged in the optical-electronic-optical transmission path. This allows the object region to be visualized for an observer in the binocular tube, even during the setting process for the imaging scale $M_E$ of the optical-electronic-optical transmission path, without the observer perceiving a change in the imaging scale.

Moreover, an aspect of the invention is that, when operating the operating microscope specified above, in a first step, an image of the object region is produced in the intermediate image plane by way of an optical-electronic-optical transmission path for image information from the object region and, in a second step following the first step, an image of the object region is produced in the intermediate image plane by way of an optical transmission path for image information from the object region in the intermediate image plane, wherein the imaging scale $M_O$ of the optical transmission path is set to the imaging scale $M_E$ of the optical-electronic-optical transmission path.

BRIEF DESCRIPTION OF THE DRAWINGS

Below, the invention will be explained in more detail on the basis of the exemplary embodiments depicted schematically in the drawings, wherein.

DESCRIPTION OF EXEMPLARY EMBODIMENTS

Figure 1:
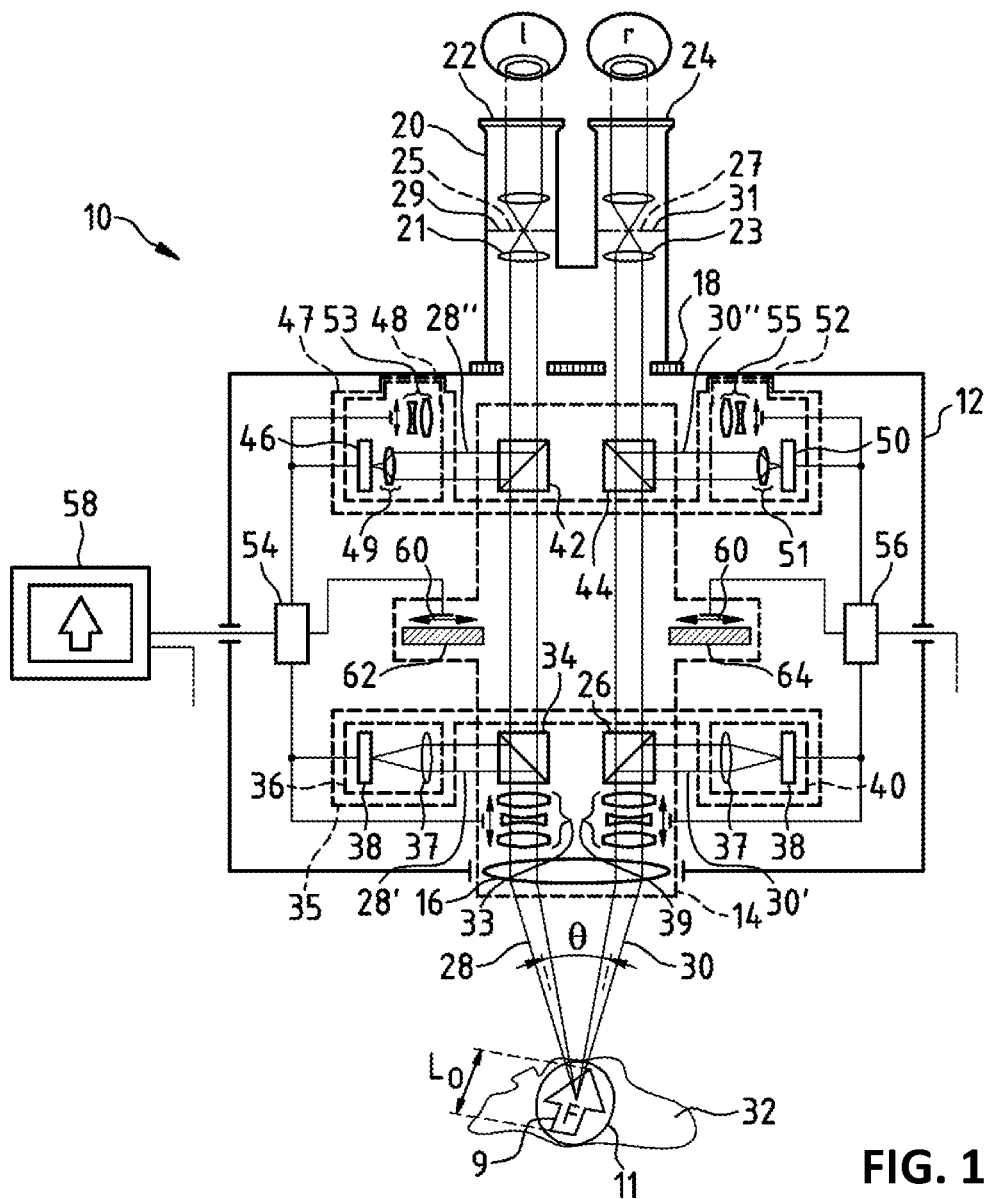
FIG. 1 shows a first operating microscope for stereoscopically visualizing an object region with a binocular tube in a first operating state.

The first stereoscopic operating microscope 10 shown in FIG. 1 has a main operating-microscope body 12, in which a switchable imaging optical unit 14 with a main microscope objective system 16 is accommodated. It has a binocular tube 20, which is connected to the main operating-microscope body 12 at an interface 18 and comprises a first and a second eyepiece 22, 24 for a left and right eye 72, 74 of an observer. The main microscope objective system 16 in the operating microscope 10 is passed through by a first optical object region imaging beam path 28 and a second optical object region imaging beam path 30 from an object region 32.

The imaging optical unit 14 contains a zoom system 33 that is arranged in the first optical object region imaging beam path 28 and it has an output coupling beam splitter 34 that is arranged on the side of the main microscope objective system 16 distant from the object region 32, the output coupling beam splitter decoupling some of the observation light from the first optical object region imaging beam path 28 in order to feed the observation light from the object region to the electronic image capture device 35 along an image sensor beam path 28'. The image capture device 35 includes a first image capture assembly 36 with an objective lens system 37 and an image sensor 38 and also a second image capture assembly 40 with an object lens system 37 and an image sensor 38.

Moreover, the imaging optical unit 14 has a zoom system 39 that is arranged in the second optical object region imaging beam path 30 on the side of the main microscope objective system 16 distant from the object region 32 and the imaging optical unit has a further output coupling beam splitter 26, which serves to feed some of the observation light from the object region 32 to the image sensor 38 of the image capture device 35 along an image sensor beam path 30' by virtue of the light being decoupled from the second optical object region imaging beam path 30.

In the imaging optical unit 14 there is a first input coupling beam splitter 42 and a second input coupling beam splitter 44. By way of the input coupling beam splitters 42, 44, display information that is displayed on a first display 46 of a display assembly 48 of a display device 47 and on a second display 50 of a display assembly 52 of the display device 47 can be overlaid in a display imaging beam path 28'', 30'' on the image of the object region 32 in the first optical object region imaging beam path 28 and in the second optical object region imaging beam path 30. To this end, the displays 46, 50 of the display assemblies 48, 52 of the display device 47 typically contain a "digital micromirror device" (DMD), which facilitates a fast interchange of images displayed therewith.

The input coupling beam splitters 42, 44 allow display information in particular, for example in the form of three-dimensional angiography data obtained pre-surgery, to be overlaid on the image of the object region 32, which is fed to the eyepiece 22 and the eyepiece 24 of the binocular tube 20.

For this, the display area of the displays 46, 50 of the display assemblies 48, 52 is in each case transferred by a first display lens group 49 and by a second display lens group 51 into a parallel beam path and imaged with the tube lenses 21, 23 into the left and right intermediate image plane 25, 27 of the binocular tube 20. There, it can be observed by the observer with the left and right eye 72, 74, respectively. The intermediate image in the left and right intermediate image plane 25, 27 is delimited by an eyepiece field stop 29, 31 in the binocular tube 20. Each display lens group 49, 51 in each case contains lenses 53, 55, which are selectively arrangeable in the beam path to the input coupling beam splitter 42, 44 or outside of the beam path. The lenses 53, 55 allow the imaging scale of the images of the display areas of the displays 46, 50 in the left and right intermediate image plane 25, 27 to be varied. This imaging scale is determined by the ratio $f_D/f_T$ of the focal length $f_D$ of the display lens group 49, 51 and the focal length $f_T$ of the tube lenses 21, 23.

For the purposes of actuating the displays 46, 50, the operating microscope 10 contains a first image processing and control device 54 embodied as an image processing and control device and a further image processing and control device 56 embodied as an image processing and control device, which can be connected to an external computer unit (not shown).

In order to visualize the images of the object region 32 that are captured with the image capture devices 35 from the first and second optical object region imaging beam path 28, 30, there is an image reproducing device 58, which is typically embodied as a 3D monitor and connected to the image processing and control device 56, in the operating microscope 10.

The imaging optical unit 14 of the operating microscope 10 contains a switchable optical assembly in the form of a shutter element 62 and a switchable optical assembly in the form of a shutter element 64. The shutter elements 62, 64 can be displaced by a drive (not shown) in a way corresponding to the double-headed arrow 60. It is possible with the shutter elements 62, 64 to selectively clear or block the first and/or second optical object region imaging beam path 28, 30 on the side of the output coupling beam splitter 34, 26 that is facing away from the main microscope objective system 16.

The image processing and control device 54 and the image processing and control device 56 are each coupled to the switchable optical assembly by way of an electrical control line. The image processing and control devices 54, 56 each comprise a data processing stage. The image processing and control device 54 receives the switching state of the shutter element 62 and the image processing and control device 56 receives the switching state of the shutter element 64.

In the first operating state of the operating microscope shown in FIG. 1, the imaging optical unit 14 is switched such that the shutter element 62 and the shutter element 64 clear the first optical object region imaging beam path 28 and the second optical object region imaging beam path 30. Then, the optical object region imaging beam paths 28 and 30 from the object region 32 that pass through the main microscope objective system 16 are respectively fed to the first and second eyepiece 22, 24 of the binocular tube 20 in the operating microscope 10.

Figure 2:
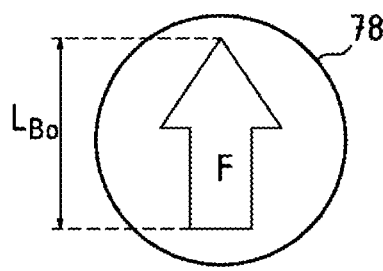
FIG. 2 shows the image field in a left and right intermediate image plane of the operating microscope in the first operating state.

In the left and right intermediate image plane 25, 27 of the operating microscope, an object 9 with the length $L_O$ in the object field 11, identified in FIG. 1, in the object region 32 is visualized in an optical image field 78, shown in FIG. 2, with an imaging scale $M_O = L_{BO}/L_O$, which is defined by the assemblies of the optical transmission paths from the object region 32 into the left and right intermediate image plane 25, 27.

Figure 3:
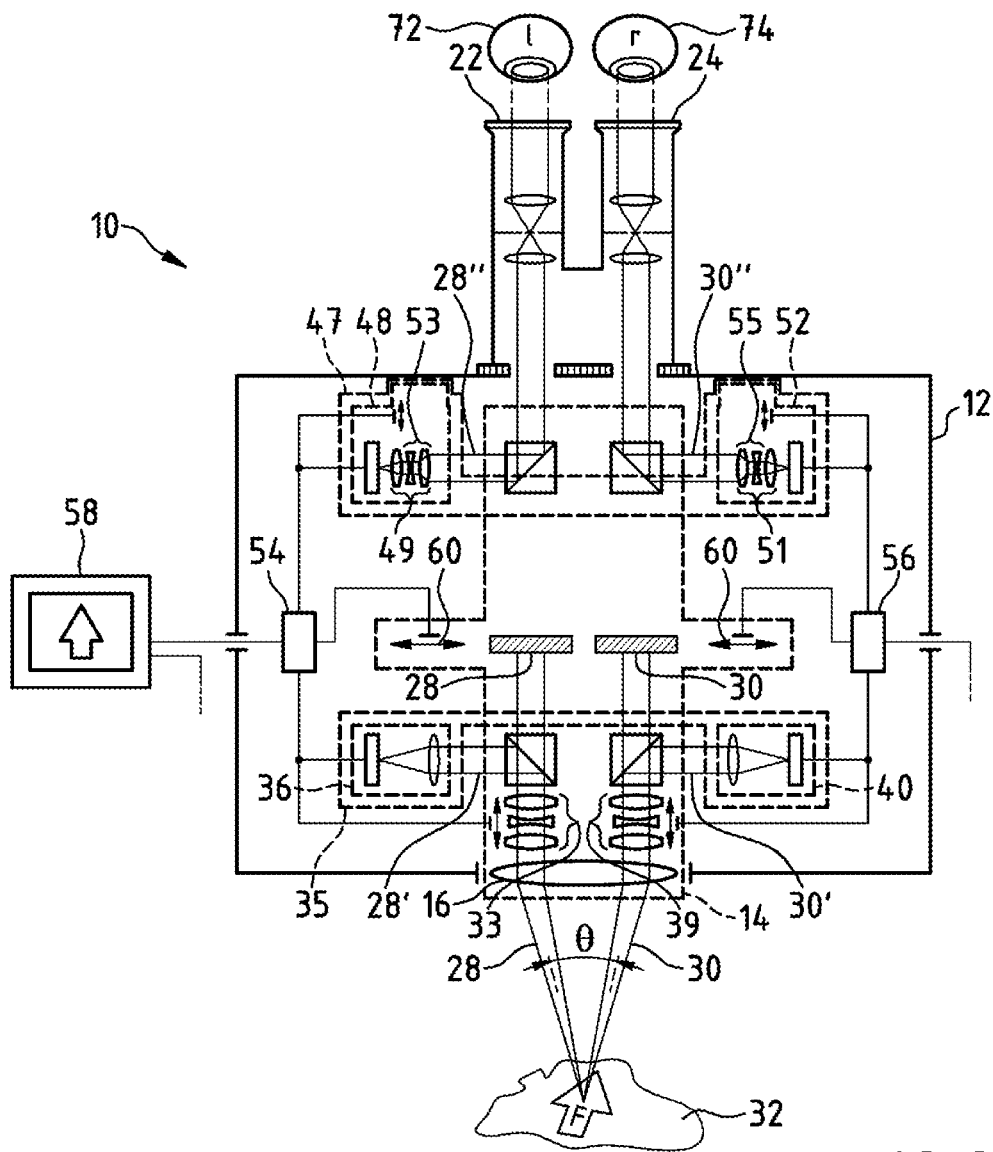
FIG. 3 shows the first operating microscope in a second operating state.

FIG. 3 shows the operating microscope 10 in a further operating state, in which the shutter element 62 and the shutter element 64 block the first optical object region imaging beam path 28 and the second optical object region imaging beam path 30. Here, an image of the object region 32 that is captured with the image capture assemblies 36 and 40 of the image capture device 35 and displayed by the displays 46, 50 in the display assemblies 48, 52 can be respectively fed to the first and second eyepiece 22, 24 of the binocular tube 20 in the operating microscope 10.

The image capture assembly 36 of the image capture device 35 can capture a left stereoscopic partial image of the object region 32 using a beam path that is decoupled from the first optical object region imaging beam path 28. Using the image capture assembly 40 of the image capture device 35, it is possible to record a right stereoscopic partial image of the object region 32 using a beam path that is decoupled from the second optical object region imaging beam path 30. The optical axes of the first optical object region imaging beam path 28 and of the second optical object region imaging beam path 30 include a stereo angle θ. This makes it possible to stereoscopically visualize the object region 32 with the operating microscope 10 even if the first optical object region imaging beam path 28 and the second optical object region imaging beam path 30 are blocked by the shutter elements 62, 64. To this end, the left stereoscopic partial image in the binocular tube 20 is then produced with the display 46 in the display assembly 48, and the right stereoscopic partial image with the display 50 in the display assembly 52, of the display device 47.

Figure 4:
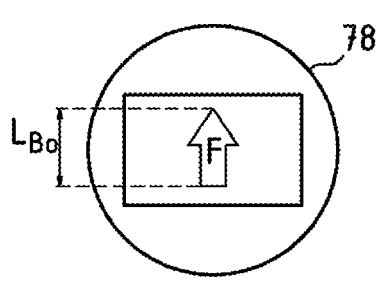
FIG. 4 shows the image field in the left and right intermediate image plane of the first operating microscope in the second operating state.

Then, in the left and right intermediate image plane 25, 27 of the operating microscope 10 and as shown in FIG. 4, the object 9 in the object field 11, identified in FIG. 1, in the object region 32 is visualized in a region corresponding to the image field 78 with an imaging scale $M_E = L_{Be}/L_O$, which is defined by the assemblies of the optical-electronic-optical transmission paths from the object region 32 into the left and right intermediate image plane 25, 27.

It should be noted that the operating microscope 10 allows the display not only of an image of the object region 32 on the displays 46, 50 of the display device but also of additional information, in particular image information such as angiography data, endoscope images, x-ray recordings or else MRI images of a patient, which, in the image processing and control device 54, 56, are combined by electronic mixing with the image of the object region 32 captured by way of the image capture device 35.

Figure 5:
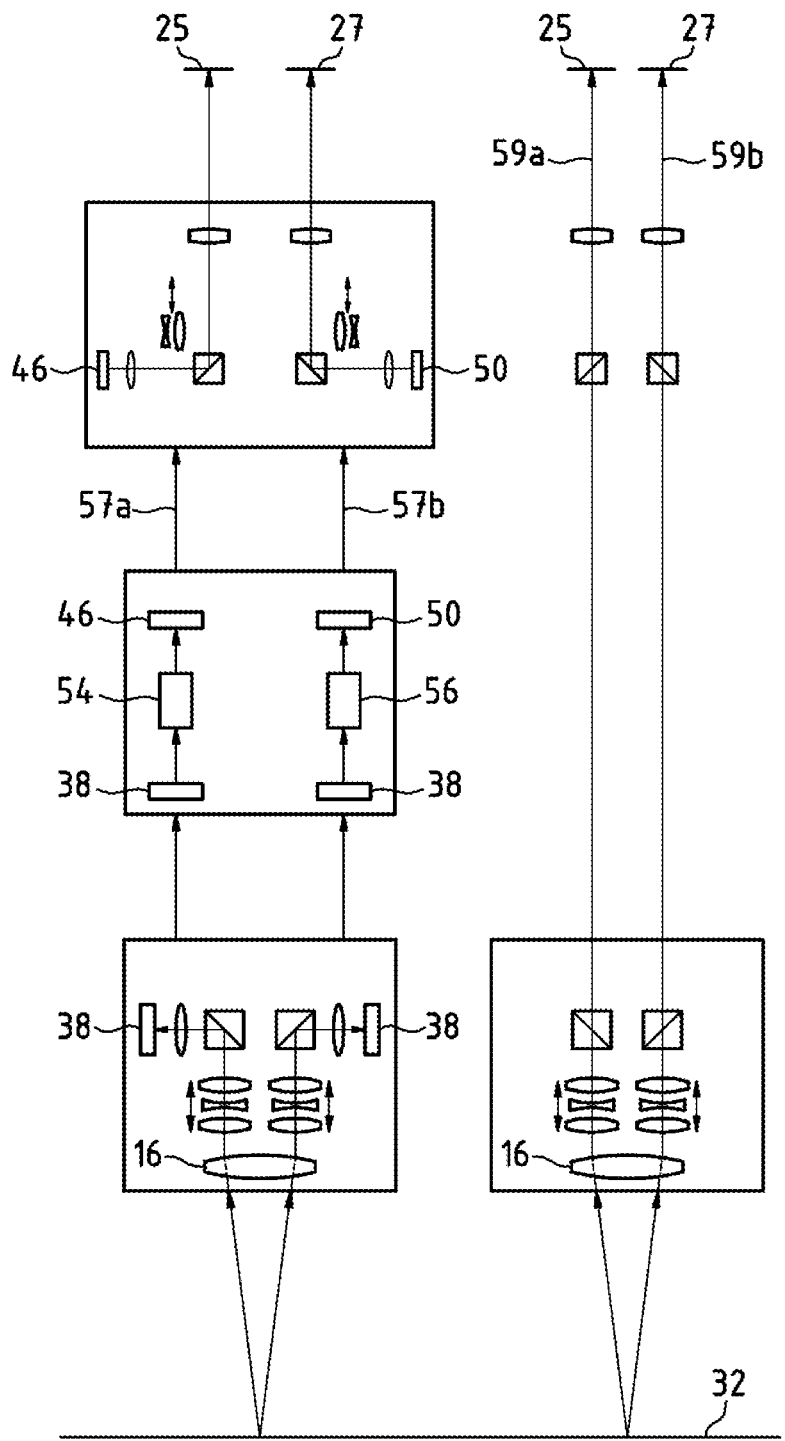
FIG. 5 shows an optical transmission path and an optical-electronic-optical transmission path in the first operating microscope.

FIG. 5 shows the optical transmission paths 57a, 57b and the optical-electronic-optical transmission paths 59a, 59b in the first operating microscope 10, with which an image of the object region having the imaging scale $M_O = L_{BO}/L_O$ and the imaging scale $M_E = L_{Be}/L_O$, respectively, is respectively provided as image information in the intermediate image plane 25 and 27.

The operating microscope 10 contains an imaging scale setting device which comprises the image processing and control device 54, 56, the lenses 53, 55 and the zoom system 33, 39.

This imaging scale setting device serves to ensure that an observer is provided with the image of the object region 32 with the same imaging scale $M_O = M_E$ in the first and the second eyepiece 22, 24 when switching the operating microscope 10 from the first operating state, in which an image of the object region 32 is produced in the intermediate image plane 25, 27 with the optical object region imaging beam path 28, 30 by way of the optical transmission paths 57a, 57b, into the further operating state, in which an image of the object region 32 is produced in the intermediate image plane 25, 27 by way of the optical-electronic-optical transmission paths 59a, 59b. The imaging scale setting device in the operating microscope 10 is also embodied to set the imaging scale $M_O$ of the optical transmission paths 57a, 57b to the imaging scale $M_E$ of the optical-electronic-optical transmission paths 59a, 59b when switching the operating microscope 10 from the further operating state, in which image information from the object region 32 is provided in the intermediate image plane 25, 27 by way of the optical-electronic-optical transmission paths 59a, 59b, into the first operating state, in which an image of the object region 32 is produced in the intermediate image plane 25, 27 with the optical object region imaging beam path 28, 30 by way of the optical transmission paths 57a, 57b.

Figure 6:
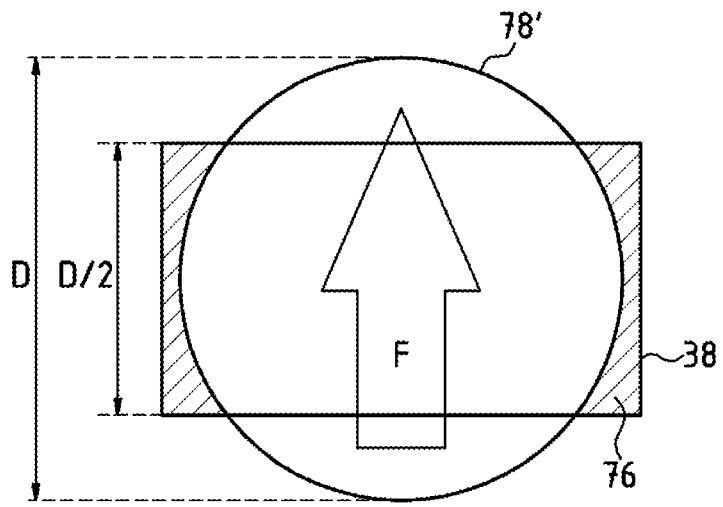
FIG. 6 shows the light-sensitive area of an image sensor in the operating microscope.

FIG. 6 shows the light-sensitive area 76 of an image sensor 38 in the operating microscope 10, and the circular image field 78' of the object region image with the diameter D on this area 76.

Figure 7:
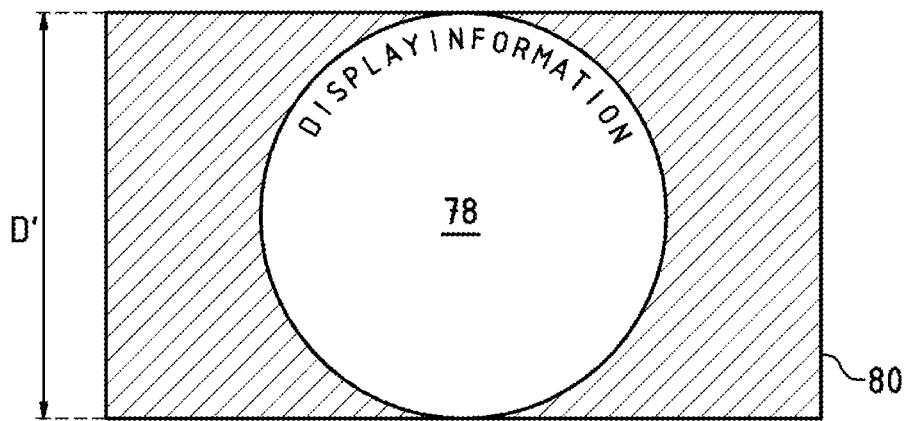
FIG. 7 shows the image of a display area of a display in an intermediate image plane of the operating microscope in a first operating state.

In FIG. 7, the image 80 of the display area of the display 46 in the intermediate image plane 25 of the operating microscope 10 is shown if the lenses 53 of the display lens group 49 are arranged in the beam path imaging the display area of the display 46 in the intermediate image plane 25 of the operating microscope 10.

A corresponding statement applies for the image of the display area of the display 50 in the intermediate image plane 27 of the operating microscope 10 if the lenses 55 of the display lens group 51 are situated in the beam path imaging the display area of the display 50 in the intermediate image plane 25 of the operating microscope 10.

The image field 78 of the optical imaging beam path with the diameter D' in the intermediate image plane 25, 27 is covered here by the image 80 of the display area of the display 46 or of the display 50. This setting of the display lens group 49, 51 is suitable for visualizing display information of the display 46, 50 in the intermediate image plane 25, 27 when the operating microscope 10 is operated in an operating state for observing the object region 32 through the first and second eyepiece 22, 24 with an optical object region imaging beam path 28, 30.

Figure 8:
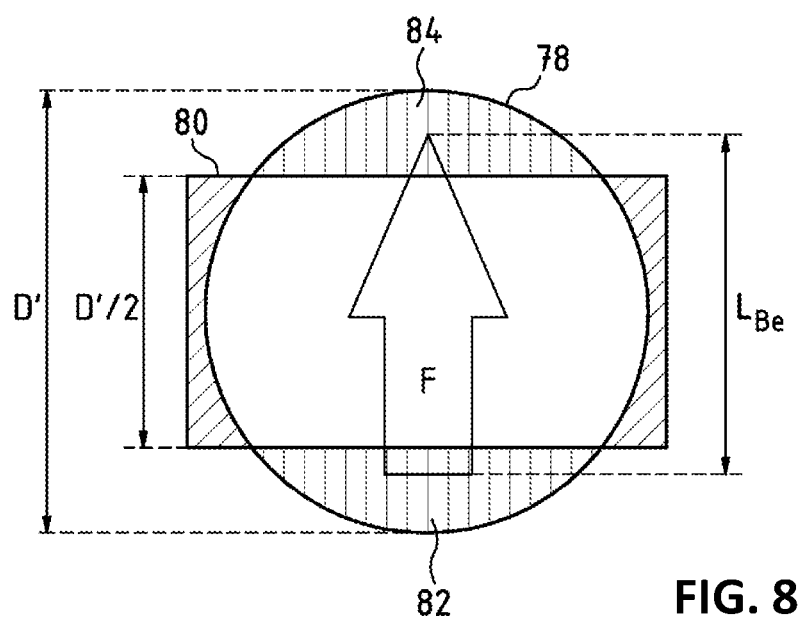
FIG. 8 shows the image of a display area of a display in an intermediate image plane of the operating microscope in a second operating state.

FIG. 8 shows the image 80 of the display area of the display in the intermediate image plane 25 in an operating state of the operating microscope 10 in which the lenses 53 of the display lens group 49 are arranged outside of the beam path imaging the display area of the display 46 into the intermediate image plane 25 of the operating microscope 10. Here, the diameter D' of the image field 78 once again exceeds the length of the narrow side of the display area of the display 46 by a factor of two.

A corresponding statement applies for the image of the display area of the display 50 in the intermediate image plane 27 of the operating microscope 10 if the lenses 55 of the display lens group 51 are arranged outside of the beam path imaging the display area of the display 50 in the intermediate image plane 25 of the operating microscope 10.

This setting of the display lens group 49, 51 is suitable for visualizing display information of the display 46, 50 in the intermediate image plane 25, 27 if the operating microscope 10 is operated in an operating state for observing the object region 32 through the eyepieces 22, 24 with an object region imaging beam path 28, 30 that is only fed to the image capture device 35, the shutter elements 62, 64 suppressing the passage of observation light into the intermediate image planes 25, 26 in the binocular tube 20 in the operating state and the image of the object region 32 captured with the image capture assemblies 36 and 40 of the image capture device 35, processed in the data processing stage of the respective image processing and control device 54, 56 and displayed at the displays 46, 50 of the display device 47 being respectively fed to the first and second eyepiece 22, 24 of the binocular tube 20 in the operating state. This is because, in this setting, the image of the display area of a display 46, 50 can be produced in the intermediate image plane 25, 27 with a greater number of pixels than allowed by the setting of the operating microscope 10 explained on the basis of FIG. 6.

In the operating microscope 10, the display lens groups 49, 51 on the display areas of the displays 46, 50 are matched to one another in such a way that, when switching the operating microscope 10 from the first operating state, in which the object region 32 is imaged into the left and right intermediate image plane 25, 27 by way of a first and by way of a second optical object region imaging beam path 28, 30, into the further operating state, in which an image of the object region 32 that is captured by the image capture assemblies 36 and 40 of the image capture device 35 and displayed with the displays 46, 50 in the display assemblies 48, 52 is respectively fed to the first and second eyepiece 22, 24 of the binocular tube 20, the following applies for the imaging scale $M_O$ that is defined by the assemblies of the optical transmission path 57a, 57b from the object region 32 into the left and right intermediate image plane 25, 27 and for the imaging scale $M_E$ that is defined by the assemblies of the optical-electronic-optical transmission paths 59a, 59b from the object region 32 into the left and right intermediate image plane 25, 27: $M_O=M_E$.

Depending on the switching state of the shutter elements 62, 64, the imaging scale setting device in the operating microscope 10 sets the imaging scale for the display information that is visualizable in the intermediate image plane 25, 27 with the display 46, 50.

An observer perceiving black edges in the regions 82, 84 in the eyepiece 22, 24 of the binocular tube 20 because the display area of the displays 46, 50 is not imaged to there is accepted in this case.

It should be noted that, in an exemplary embodiment that is modified in relation to the exemplary embodiment of the operating microscope 10 described above, provision can be made for the display lens groups 49, 51 to facilitate continuous setting of the magnification for the image of the display areas of the displays in the intermediate image planes 25, 27.

Figure 9:
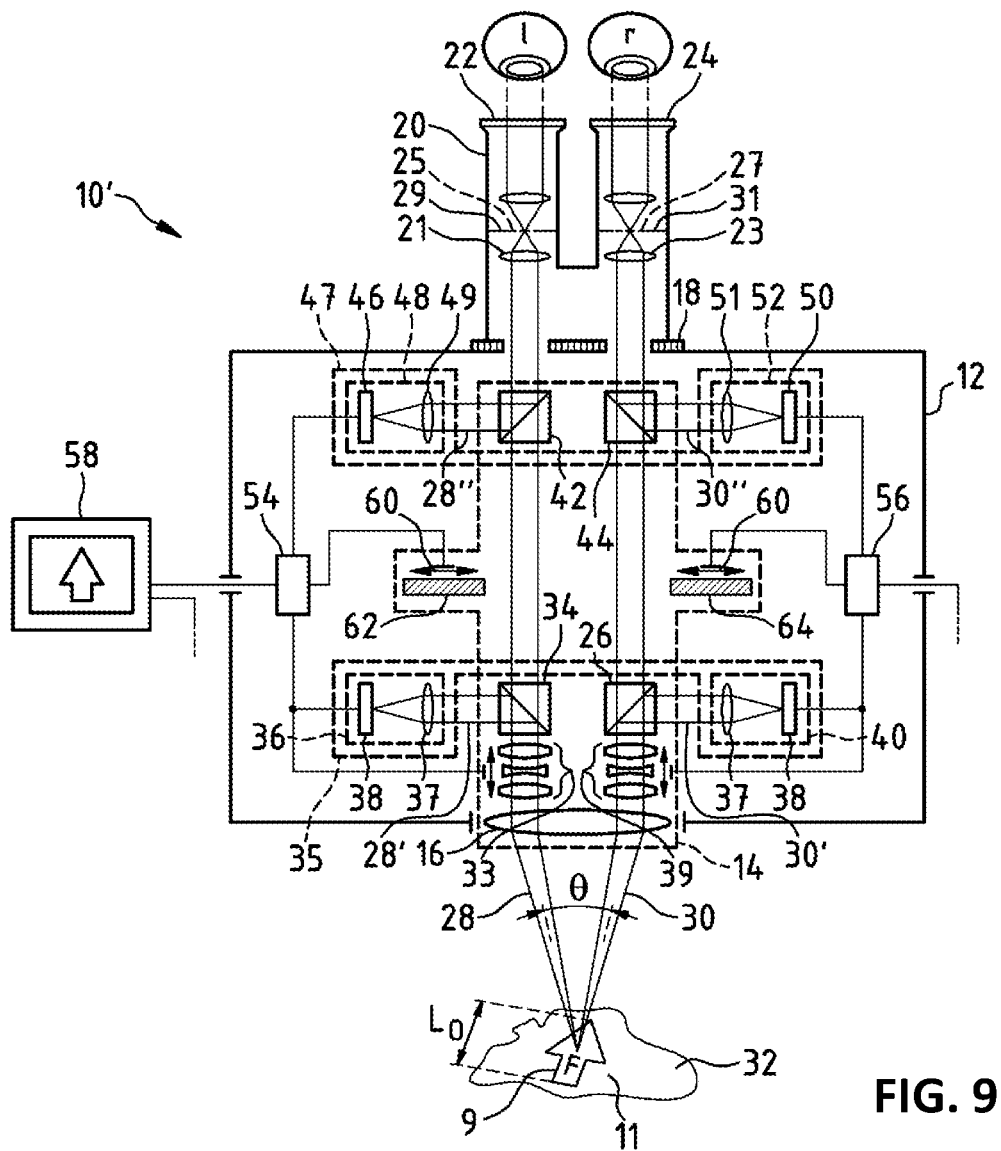
FIG. 9 shows a second operating microscope for stereoscopically visualizing an object region with a binocular tube in a first operating state.
Figure 10:
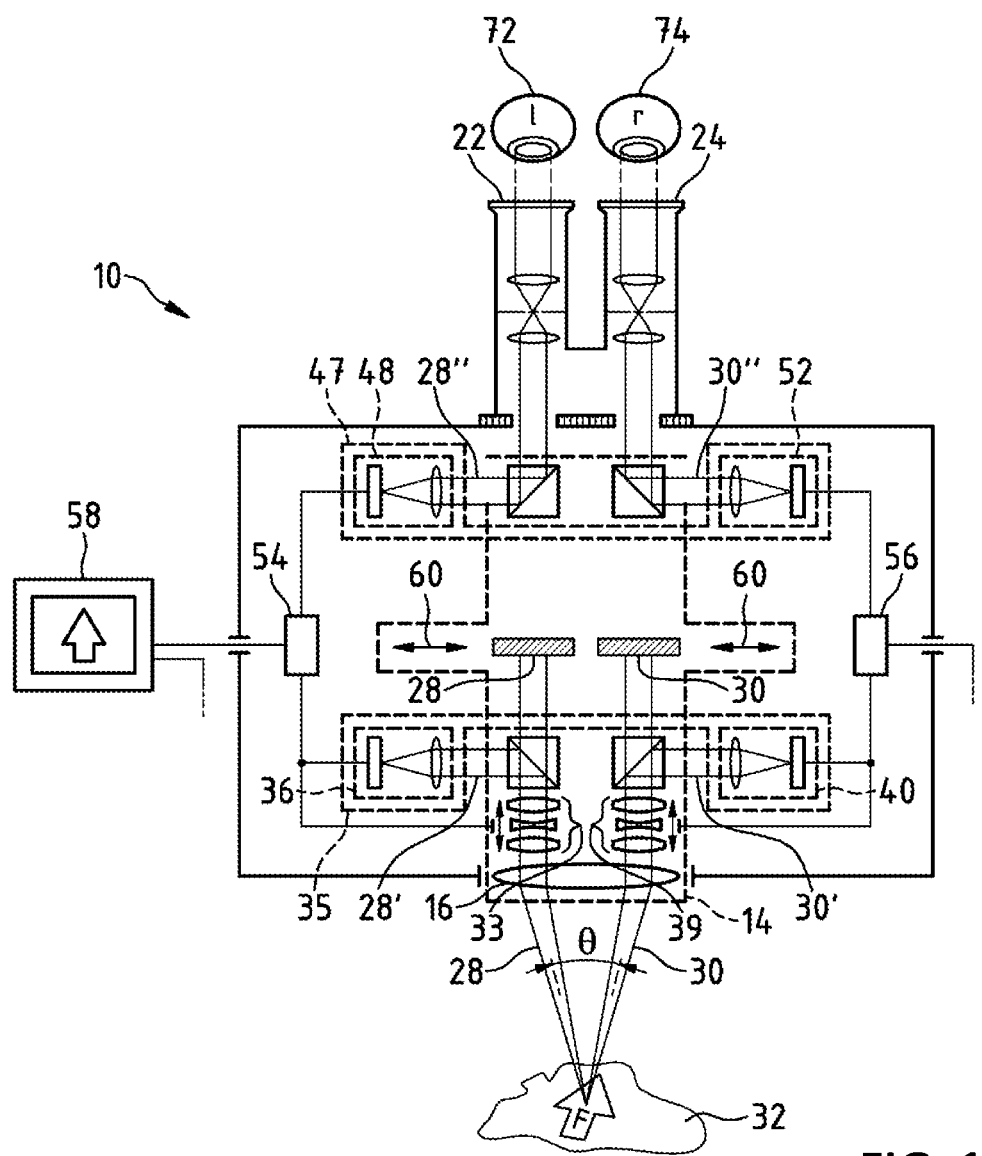
FIG. 10 shows the second operating microscope in a second operating state.

FIG. 9 shows a second operating microscope 10' for stereoscopically visualizing an object region 32 with a binocular tube 20 in a first operating state. FIG. 10 shows the second operating microscope 10' in a second operating state. Assemblies of the operating microscope 10 and of the operating microscope 10' that are identical to one another are denoted by the same reference sign. In contrast to the operating microscope 10, the operating microscope 10' does not contain adjustable display lens groups 49, 51. In the operating state shown in FIG. 8, the imaging optical unit 14 is switched such that the shutter element 62 and the shutter element 64 clear the first optical object region imaging beam path 28 and the second optical object region imaging beam path 30. Then, the first and the second eyepiece 22, 24 of the binocular tube 20 obtains an image of the object region by way of an optical transmission path. Then, the optical object region imaging beam paths 28 and 30 from the object region 32 that pass through the main microscope objective system 16 are respectively fed to the first and second eyepiece 22, 24 of the binocular tube 20 in the operating microscope 10'.

In the operating state of the operating microscope 10' shown in FIG. 10, the shutter element 62 and the shutter element 64 block the first optical object region imaging beam path 28 and the second optical object region imaging beam path 30. Here, the image of the object region 32 that is captured by the image capture assemblies 36 and 40 of the image capture device 35 and displayed by way of the displays 46, 50 of the display device 47 is respectively fed to the first and second eyepiece 22, 24 of the binocular tube 20 in the operating microscope 10 along an optical-electronic-optical transmission path.

Figure 11:
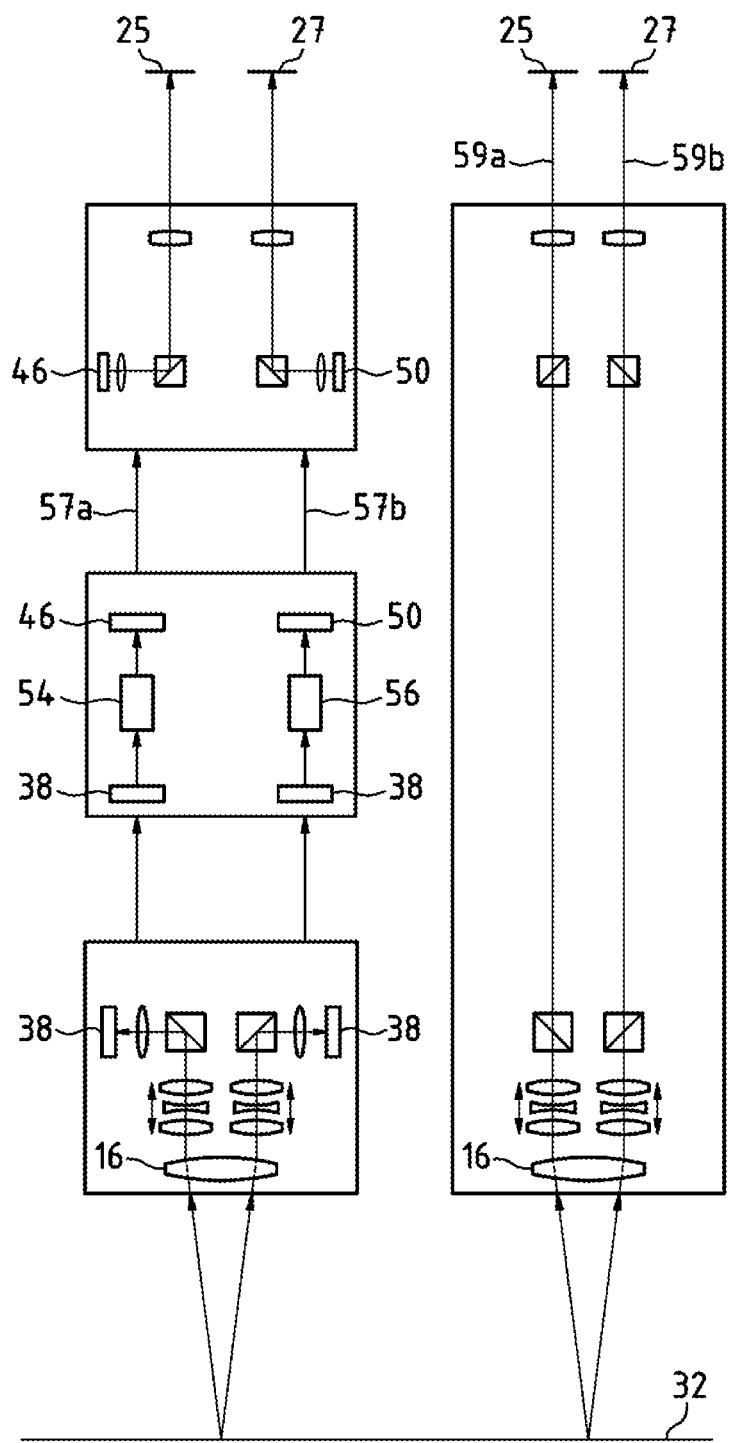
FIG. 11 shows an optical transmission path and optical-electronic-optical transmission path in the second operating microscope.

FIG. 11 shows the optical transmission paths 57a, 57b and the optical-electronic-optical transmission paths 59a, 59b in the first operating microscope 10, with which an image of the object region having the imaging scale $M_O=L_{BO}/L_O$ and the imaging scale $M_E=L_{Be}/L_O$, respectively, is respectively provided in the intermediate image plane 25 and 27.

The operating microscope 10', too, contains an imaging scale setting device which comprises the image processing and control device 54, 56, the lenses 53, 55 and the zoom system 33, 39.

Here, the image processing and control device 54, 56 in the operating microscope 10' in turn ensures that an observer is provided with the image of the object region 32 with the same imaging scale $M_O=M_E$ in the first and the second eyepiece 22, 24 when switching the operating microscope 10 from the first operating state, in which an image of the object region 32 is produced in the intermediate image plane 25, 27 with the optical object region imaging beam path 28, 30 by way of the optical transmission paths 57a, 57b, into the further operating state, in which an image of the object region 32 is produced in the intermediate image plane 25, 27 by way of the optical-electronic-optical transmission paths 59a, 59b. The imaging scale setting device in the operating microscope 10 is also embodied to set the imaging scale $M_O$ of the optical transmission paths 57a, 57b to the imaging scale of the optical-electronic-optical transmission paths 59a, 59b when switching the operating microscope 10 from the further operating state, in which an image of the object region 32 is produced in the intermediate image plane 25, 27 by way of the optical-electronic-optical transmission paths 59a, 59b, into the first operating state, in which an image of the object region 32 is produced in the intermediate image plane 25, 27 with the optical object region imaging beam path 28, 30 by way of the optical transmission paths 57a, 57b.

Figure 12:
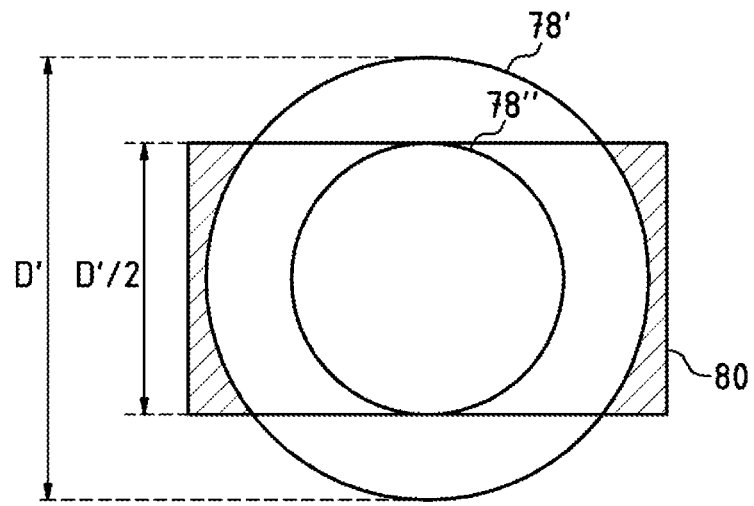
FIG. 12 shows image fields in the case of different settings of a zoom system in the operating microscope.

FIG. 12 shows the circular image field 78' of the object region image with the diameter D' on this area 76 if the image of the object region 32 is displayed in the intermediate image planes 25, 27 with the optical object region imaging beam path 28, 30 by way of the optical transmission paths 57a, 57b.

Figure 13:
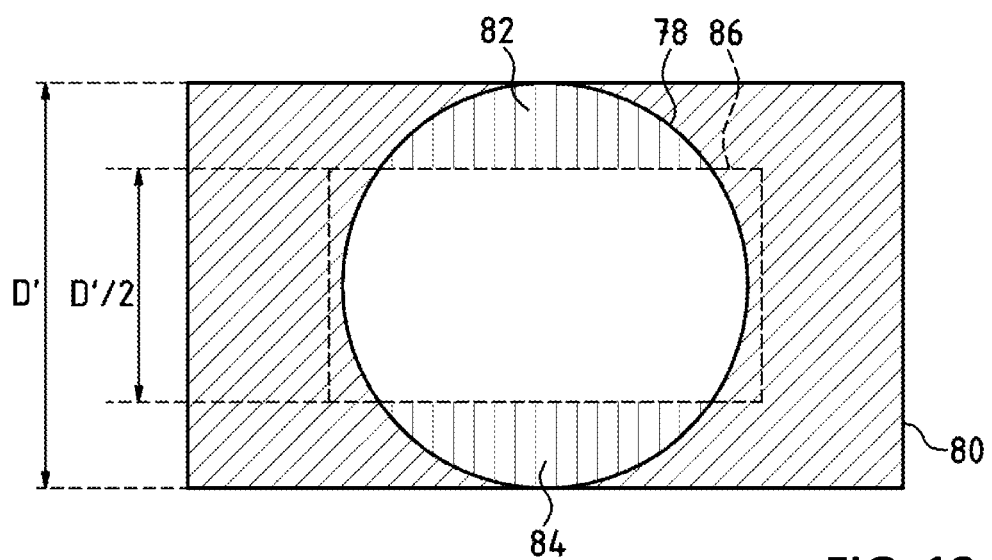
FIG. 13 shows the image of a display area of the display in the second operating microscope in a first setting of the zoom system.

FIG. 13 shows the image 80 of the display area of the display 46 in the intermediate image plane 25 of the operating microscope in 10'. In the operating state of FIG. 9, in which the optical object region imaging beam path 28, 30 is guided to the eyepieces 22, 24, the image of the object region 32 produced in the image field 78 with the first optical object region imaging beam path 28 and the second optical object region imaging beam path 30 in the intermediate image plane 25, 27 covers the image 80 of the display area of the display 46 or of the display 50, produced with the display lens group 49 or 51, respectively, in the object field 11.

If the operating microscope 10' is switched from the first operating state into the further operating state, the image processing and control device 54, 56 obtains the setting of the zoom system 33, 39 as an operand. Then, the image processing and control device 54, 56 ascertains the imaging scale $M_O$ of the optical transmission path 57a, 57b in the operating microscope 10' therefrom, with the displays 46, 50 in the display assemblies 48, 52 being switched to be dark. So that the imaging scale $M_E$ of the optical-electronic-optical transmission paths 59a, 59b corresponds to the imaging scale $M_O$ of the optical transmission paths 57a, 57b, it is necessary here for an image display 86 to be provided in the intermediate image planes 25, 27 by the displays 46, 50, the image display reducing the image captured with the image sensors 38 of the image capture device 35 in the operating microscope 10', wherein then no image information is displayed by the displays 46, 50 in the regions 82, 84 of the intermediate image planes 25, 27. Such regions 82, 84 without image information in an intermediate image plane 25, 27 are perceived as black edges by an observer at the eyepieces 22, 24.

In order to avoid such regions 82, 84, the image processing and control device 54, 56 causes an adjustment of the zoom system 33, 39 in the first optical object region imaging beam path 28 and in the second optical object region imaging beam path 30.

Figure 14:
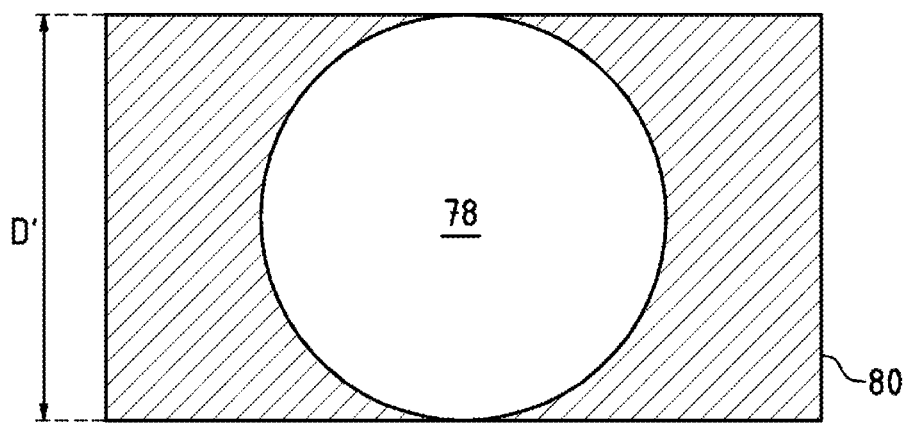
FIG. 14 shows the image of a display area of the display in the second operating microscope in a different setting of the zoom system.

As shown in FIG. 12, the zoom systems 33, 39 in the first optical object region imaging beam path 28 and in the second optical object region imaging beam path 30 are adjusted in such a way to this end that the image sensors 38 of the image capture device 35 capture the object field 11 entirely as an image field 78". In accordance with the adjustment of the zoom system 33, 39, the image processing and control device 54, 56 then rescales the image data fed to the displays 46, 50 in such a way that an image of the object region 32 is produced in the intermediate image planes 25, 27 by the display 86 of the displays 46, 50 shown in FIG. 14, the imaging scale $M_O$ of the image corresponding to the imaging scale $M_E$ and the image, like the image 80 visible in FIG. 13, covering the image field 78 of the optical transmission paths 57a, 57b in an intermediate image plane 25, 27.

When switching from the first operating state into the further operating state, the operating microscope 10' for the stereoscopic visualization of an object region 32 can be operated in a first switchover operating mode and in a second switchover operating mode that differs from the first switchover operating mode.

In the first switchover operating mode, a display of display information at the displays 46, 50 of the display device 47 is suppressed for the duration of the switchover when blocking or clearing the first optical object region imaging beam path 28 and the second optical object region imaging beam path 30 by the shutter elements 62, 64. Here, display information by the displays 46, 50 in the intermediate image planes 25, 27 is only provided to an observer when adapting the imaging scale $M_E$ of the optical-electronic-optical transmission paths 59a, 59b to the imaging scale $M_O$ of the optical transmission path 57a, 57b in the operating microscope 10' or when adapting the imaging scale of the optical transmission path 57a, 57b in the operating microscope 10' to the imaging scale $M_E$ of the optical-electronic-optical transmission paths 59a, 59b in the operating microscope 10' has been completed.

In the second switchover operating mode, display information at the displays 46, 50 of the display device 47 is also displayed for the duration of the switchover when blocking or clearing the first optical object region imaging beam path 28 and the second optical object region imaging beam path 30 with the shutter elements 62, 64. Here, when adjusting the zoom system 33, 39 in the first optical object region imaging beam path 28 and in the second optical object region imaging beam path 30, there is a continuous rescaling of the image information, respectively adapted to the setting of the zoom system 33, 39, for the images of the object region displayed by the displays 46, 50, and so an observer does not perceive a change of the imaging scale in the eyepieces 22, 24 when the operating microscope 10' is switched from the first operating state into the further operating state.

It should be noted that provision in a modified embodiment of the operating microscopes 10, 10' described above can be made for the operating microscopes to be designed for observation of the object region through a binocular tube for a main observer and one or more binocular tubes for co-observation. Furthermore, it should be noted that the operating microscopes 10, 10' described above may also, in principle, be designed for observing the object region 32 with a monocular imaging beam path. Moreover, it should be noted that this invention also relates to operating microscopes in which only partial features of the embodiments described above are realized or in which features of the first operating microscope 10 and of the second operating microscope 10' are combined.

In summary, the following, in particular, should be noted: The invention relates to an operating microscope 10, 10' for producing an observation image of an object region 32 for an observer. The operating microscope has an eyepiece 22, 24 for observing the observation image of the object region 32 in an intermediate image plane 25, 27 and it contains an imaging optical unit 14 for producing an optical image of the object region 32 in the intermediate image plane 25, 27 by way of an optical object region imaging beam path that is guided from the object region 32 into the intermediate image plane 25, 27. In the operating microscope 10, there is a switchable optical assembly 62, 64 for selectively clearing and interrupting the optical object region imaging beam path and an image sensor 38 for capturing an image of the object region 32 by way of an optical image sensor beam path 28', 30' that is guided from the object region 32 to the image sensor 38. The operating microscope 10 has a display 46, 50 for visualizing display information in the intermediate image plane 25, 27 by way of a display imaging beam path 28", 30" and contains an image processing and control device 54, 56 for actuating the display 46, 50 and for processing and outputting image data of the image sensor 38 onto the display 46, 50. According to the invention, the operating microscope 10 comprises an imaging scale setting device for setting an imaging scale, dependent on the switching state of the optical assembly 62, 64, for the display information that is visualizable in the intermediate image plane 25, 27 by the display 46, 50.

The foregoing disclosure of the exemplary embodiments of the invention illustrates and describes the present invention. Additionally, the disclosure shows and describes only the exemplary embodiments, but, as mentioned above, it is to be understood that the invention is capable of being used in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

All publications, patents, and patent applications cited in this specification are herein incorporated by reference, and for any and all purposes, as if each individual publication, patent, or patent application were specifically and individually indicated to be incorporated by reference. In the case of inconsistencies, the present disclosure will prevail.

LIST OF REFERENCE SIGNS

9 Object
10, 10' Operating microscope
11 Object field
12 Main operating-microscope body
14 Imaging optical unit
16 Main microscope objective system
18 Interface
20 Binocular tube
21 Tube lens
22 First eyepiece
23 Tube lens
24 Second eyepiece
25 Left intermediate image plane
26 Further output coupling beam splitter
27 Right intermediate image plane
28 First object region imaging beam path
30 Second object region imaging beam path
28', 30' Image sensor beam path
28", 30" Display imaging beam path
29 Eyepiece field stop
31 Eyepiece field stop
32 Object region
33 Zoom system/magnification interchange system
34 Output coupling beam splitter
35 Image capture device
36 First image capture assembly
37 Objective lens system
38 Image sensor
39 Zoom system/magnification interchange system
40 Second image capture assembly
42 First input coupling beam splitter
44 Second input coupling beam splitter
46 First display
47 Display device
48 Display assembly
49 First display lens group
50 Second display
51 Second display lens group
52 Display assembly
53 Lens/optical magnification interchange system
54 Image processing and control device
55 Lens/optical magnification interchange system
56 Image processing and control device
57a, 57b Optical transmission path
58 Image reproducing device
59a, 59b Optical-electronic-optical transmission path
60 Double-headed arrow
62 Shutter element/switchable optical assembly
64 Shutter element/switchable optical assembly
72 Left eye
74 Right eye
76 Light-sensitive area
78 Circular image field
78' Image field
78" Image field
80 Image
82 Region with black edges
84 Region with black edges
86 Image display

The invention claimed is:
1. An operating microscope for producing an observation image of an object field of an object region for at least one observer, the operating microscope comprising:
an eyepiece for observing a first observation image of an object field of an object region in an intermediate image plane;
an imaging optical unit configured to produce the first observation image of the object field of the object region in the intermediate image plane;
an optical object region imaging beam path being guided from the object region to the intermediate image plane along an optical transmission path;
a switchable optical assembly configured to selectively clear, interrupt, or clear and interrupt the optical object region imaging beam path, the switchable optical assembly clearing the optical transmission path in a first switching state and interrupting the optical transmission path in a further switching state that differs from the first switching state;
at least one image sensor configured to capture a further observation image of the object region being projected along an optical image sensor beam path, the optical image sensor beam path being guided from the object region to the at least one image sensor;
a display configured to project the further observation image of the object region in the intermediate image plane, the further observation image being projected along a display imaging beam path;
an image processing and control device configured to:
actuate the display;
process and output the further observation image of the object region of the image sensor onto the display, thereby providing an optical-electronic-optical transmission path; and
overlay display information onto the further observation image, the display information being visualizable in the intermediate image plane;
an imaging scale setting device configured to set an imaging scale, dependent on the switching state of the optical assembly, for the display information that is visualizable in the intermediate image plane by the display; and
a coupler configured to couple the switchable optical assembly and the imaging scale setting device,
wherein the imaging scale setting device has an optical magnification interchange system that is arranged in the image sensor beam path,
wherein the magnification interchange system is a constituent part of the imaging optical unit for producing the first observation image of the object field of the object region in the intermediate image plane projected along the optical object region imaging beam path,
wherein, when switching from the first switching state into the further switching state of the switchable optical assembly, the imaging scale setting device sets an imaging scale of the optical-electronic-optical transmission path to the imaging scale of the optical transmission path in the first switching state of the switchable optical assembly and, by setting the optical magnification interchange system, causes the at least one image sensor to capture the object field entirely as an image field,
wherein the display information in the intermediate image plane is overlaid onto the further observation image of the observation region captured by the at least one image sensor covers the image field of the optical transmission path in the first switching state of the switchable optical assembly, the display information being visualized with the display in the display imaging beam path in the further switching state of the switchable optical assembly, and wherein the image processing and control device rescales the further observation image of the object field supplied to the display in the further switching state when the further observation image of the object field is displayed in the object region on the display in the intermediate image plane, the imaging scale of the further observation image corresponding to the imaging scale of the first observation image.

2. The operating microscope as claimed in claim 1, wherein the imaging scale setting device includes a data processing stage integrated into the image processing and control device.

3. The operating microscope as claimed in claim 1, wherein the switchable optical assembly for selectively clearing and interrupting the optical object region imaging beam path is configured as a switchable shutter.

4. An operating microscope for producing an observation image of an object field of an object region for at least one observer, the operating microscope comprising:
    an eyepiece for observing a first observation image of an object field of an object region in an intermediate image plane;
    an imaging optical unit configured to produce the first observation image of the object field of the object region in the intermediate image plane;
    an optical object region imaging beam path being guided from the object region to the intermediate image plane along an optical transmission path;
    a switchable optical assembly configured to selectively clear, interrupt, or clear and interrupt the optical object region imaging beam path, the switchable optical assembly clearing the optical transmission path in a first switching state and interrupting the optical transmission path in a further switching state that differs from the first switching state;
    at least one image sensor configured to capture a further observation image of the object region being projected along an optical image sensor beam path, the optical image sensor beam path being guided from the object region to the at least one image sensor;
    a display configured to project the further observation image of the object region in the intermediate image plane, the further observation image being projected along a display imaging beam path;
    an image processing and control device configured to:
    actuate the display;
    process and output the further observation image of the object region of the image sensor onto the display, thereby providing an optical-electronic-optical transmission path; and
    overlay display information onto the further observation image, the display information being visualizable in the intermediate image plane;
    an imaging scale setting device configured to set an imaging scale, dependent on the switching state of the optical assembly, for the display information that is visualizable in the intermediate image plane by the display; and
    a coupler configured to couple the switchable optical assembly and the imaging scale setting device, wherein the imaging scale setting device has an optical magnification interchange system that is arranged in the image sensor beam path, wherein the magnification interchange system is a constituent part of the imaging optical unit for producing the first observation image of the object field of the object region in the intermediate image plane projected along the optical object region imaging beam path, wherein, when switching from the first switching state into the further switching state of the switchable optical assembly, the imaging scale setting device sets an imaging scale of the optical-electronic-optical transmission path to the imaging scale of the optical transmission path in the first switching state of the switchable optical assembly and, by setting the optical magnification interchange system, causes the at least one image sensor to capture the object field entirely as an image field, wherein the display information in the intermediate image plane is overlaid onto the further observation image of the observation region captured by the at least one image sensor covers the image field of the optical transmission path in the first switching state of the switchable optical assembly, the display information being visualized with the display in the display imaging beam path in the further switching state of the switchable optical assembly, wherein the image processing and control device rescales the further observation image of the object field supplied to the display in the further switching state when the further observation image of the object field is displayed in the object region on the display in the intermediate image plane, the imaging scale of the further observation image corresponding to the imaging scale of the first observation image, and wherein the magnification interchange system is an afocal zoom system.

5. A method of operating an operating microscope for producing at least one observation image of an object field in an object region for at least one observer, the method comprising:
    providing an eyepiece for observing a first observation image of an object field of an object region in an intermediate image plane;
    producing the first observation image of the object field in the object region in the intermediate image plane with an imaging optical unit;
    guiding an optical object region imaging beam path from the object region into the intermediate image plane along an optical transmission path;
    selectively clearing, interrupting, or clearing and interrupting the optical object region imaging beam path with a switchable optical assembly, the optical assembly clearing the optical transmission path in a first switching state and interrupting the optical transmission path in a further switching state that differs from the first switching state;
    capturing a further observation image of the object region with at least one image sensor through an optical image sensor beam path that is guided from the object region to the at least one image sensor;
    visualizing display information in the intermediate image plane with a display along a display imaging beam path;
    producing the further observation image of the object region in the intermediate image plane with an image processing and control device, the image processing and control device being configured to actuate the display and to process and output the further observation image of the object region of the image sensor onto the display, thereby providing an optical-electronic-optical transmission path;

setting, depending on a switching state of the optical assembly, an imaging scale with an imaging scale setting device for the display information that is visualizable in the intermediate image plane with the display;

arranging an optical magnification interchange system of the imaging scale setting device in the image sensor beam path;

projecting the further observation image of the object region along the optical object region imaging beam path in the intermediate image plane with the imaging optical unit, the magnification interchange system being a constituent part of the imaging optical unit;

producing the first observation image of the object region in the intermediate image plane along the optical transmission path into the intermediate image plane in a first switching state;

producing the further observation image of the object region in the intermediate image plane along the optical-electronic-optical transmission path into the intermediate image plane in the further switching state;

setting the imaging scale of the optical-electronic-optical transmission path to the imaging scale of the optical transmission path when switching from the first switching state into the further switching state of the switchable optical assembly;

setting the optical magnification interchange system to capture the object field entirely as an image field with the at least one image sensor;

overlaying display information onto the further observation image captured by the at least one image sensor, the display information covering the image field of the first observation image in the intermediate image plane in the first switching state of the switchable optical assembly; and rescaling, in the further switching state, the imaging scale of the further observation image of the object region to the imaging scale of the further observation image that corresponds to the imaging scale of the first observation image in the intermediate image plane.

6. The method as claimed in claim 5, further comprising at least one of:

suppressing the display information when setting the imaging scale of the further observation image; or matching the display information to a magnification of an optical magnification interchange system arranged in the optical-electronic-optical transmission path when setting the imaging scale of the further observation image.

* * * * *

UNITED STATES PATENT AND TRADEMARK OFFICE
CERTIFICATE OF CORRECTION

Page 1 of 1

PATENT NO. : 10,838,189 B2
APPLICATION NO. : 15/923815
DATED : November 17, 2020
INVENTOR(S) : Alois Regensburger et al.

It is certified that error appears in the above-identified patent and that said Letters Patent is hereby corrected as shown below:

On the Title Page

Item (72) change:
(72) Inventor: Alois Regensburger, Erlangen (DE)

To:
(72) Inventor: Alois Regensburger, Poxdorf (DE)

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*